United States Patent [19]

Bi

[11] 4,387,264

[45] Jun. 7, 1983

[54] DIOLEFIN MONOMER PURIFICATION PROCESS FOR ANIONIC POLYMERIZATION

[75] Inventor: Le-Khac Bi, West Chester, Pa.

[73] Assignee: Atlantic Richfield Company, Los Angeles, Calif.

[21] Appl. No.: 259,794

[22] Filed: May 4, 1981

[51] Int. Cl.³ .............................................. B01D 15/00
[52] U.S. Cl. .................................... 585/822; 585/824; 210/689
[58] Field of Search ................ 210/689; 585/802, 810, 585/822-824

[56] References Cited

U.S. PATENT DOCUMENTS

| | | |
|---|---|---|
| 2,906,793 | 9/1959 | Rowe et al. .......................... 585/822 |
| 3,240,830 | 3/1966 | Dye ...................................... 585/822 |
| 3,247,242 | 4/1966 | McGarvey et al. ................ 585/824 |
| 3,306,945 | 2/1967 | Conviser ............................. 585/823 |
| 3,969,344 | 7/1976 | Ackermann et al. ............... 210/689 |

Primary Examiner—Ivars C. Cintins

[57] ABSTRACT

An improved process for the purification of diolefin monomers for anionic polymerization is disclosed. The purification process of this invention results in polymer which exhibits excellent chain growing.

1 Claim, No Drawings

DIOLEFIN MONOMER PURIFICATION PROCESS FOR ANIONIC POLYMERIZATION

This invention relates to anionic polymerization. In one of its more specific aspects, this invention relates to an improved process for the purification of diolefin monomers for anionic polymerization.

Polymerization of diolefin monomers such as a butadiene using anionic polymerization initiators is well known. The need to purify diolefin monomers prior to introducing them into a polymerization reaction vessel is also well known. If the monomers are not purified, impurities carried into the reaction vessel with the monomers can cause complete or partial termination of the growing polymer chain. Partial termination results in a broadening of the molecular weight distribution and an overall molecular weight increase in the polymer. The effect of impurities in the reaction vessel is most easily understood in the formation of block copolymers where one monomer (e.g. styrene) is polymerized and then reacted with a second monomer (e.g. butadiene). If impurities are introduced into the reaction vessel along with the butadiene, a high percentage of "dead" polystyrene results.

To eliminate the impurities, e.g. water, inhibitor, etc., from diolefin monomers and thus reduce the percentage of dead growing polymer chains which occur during polymerization, the diolefin monomers are typically passed sequentially through a plurality of ion exchange columns packed with moleular sieve and, then, just prior to introduction into the reaction vessel, through at least one ion exchange column packed with adsorption alumina. This prior art procedure, while greatly reducing the percentage of dead growing polymer chains which occur during polymerization, typically results in a percentage of "dead" polymer considered to be too high for commercial production. Typically, more than about 2.5% dead material is considered too high for commercial production.

The present invention provides a simple and straight forward ion exchange purification process for diolefin monomers which facilitates the anionic polymerization of diolefins monomers and results in polymers which exhibit excellent chain growing.

According to this invention, there is provided, in a method of purifying diolefin monomers for anionic polymerization of the type wherein a diolefin monomer is sequentially passed through at least one ion exchange column packed with molecular sieves and at least one ion exchange column packed with adsorption alumina just prior to being introduced into the polymerization reaction vessel, the improvement comprising, after passing the diolefin monomer through the ion exchange column packed with adsorption alumina and before introducing the diolefin monomer into the polymerization reaction vessel, the step of passing the diolefin monomer through an ion exchange column packed with molecular sieves.

In a preferred embodiment, the method of this invention simply requires rearranging the order of the ion exchange columns since typically in the prior art a three column ion exchange system is employed—the first and second columns being packed with molecular sieves and the third column being packed with adsorption alumina. If this is the case, all that is required to convert to the method of this invention is to rearrange the columns by placing the column containing alumina between the two columns containing molecular sieves. No additional column is required.

In the practice of this invention any suitable molecular sieves, conventionally employed to purify diolefin monomers for anionic polymerization can be employed. Particularly suitable molecular sieves are the 3A and 4A type. Type 13X molecular sieve crystals are not suitable for use because they cause polymerization to occur. One particularly suitable brand of molecular sieves is Linde ® Adsorbants molecular sieves, Type 4A (1/16 pellets), commercially available from the Linde Division of Union Carbide Corporation.

Likewise, any suitable adsorption alumina can be employed. Particularly suitable is the adsorption alumina designated "Fisher A-540" (80-200 mesh) commercially available from Fisher Scientific Co.

The present invention is further illustrated by the following examples.

EXAMPLE I (Prior Art)

Three columns (A, B and C) of an ion exchange system used for the purification of diolefin monomers were packed with Linde ® type 4A molecular sieves, Linde ® type 4A molecular sieves and adsorption alumina ("Fisher A-540"), respectively. Each column was constructed of 2 inch diameter, schedule 40 iron pipe with brass caps and was about 5 feet long.

Butadiene (rubber grade, purchased from Matheson Gas Products) was passed sequentially through columns A, B and C. After passing through the absorption alumina in column C, about 515 mls of the purified butadiene were introduced into a polymerization reaction vessel containing polystyryl lithium anions (produced by reacting 304 mls styrene and 7.4 mls of a 1.45 M/L butyllithium initiator in about 2300 mls of cyclohexane for 20 minutes at 60° C.). The butadiene and the polystyryl lithium anions were polymerized for about 60 minutes at 60° C.

The resulting reaction product was analyzed on a Gel Permeation Chromatograph using polystyrene standards and was found to contain about 10.1% by weight "dead" polystyrene.

EXAMPLE II

The example demonstrates the method of this invention using substantially the procedure of and amounts of ingredients recited in Example I with the exception that the ion exchange columns were rearranged.

Butadiene was purified by sequentially passing it through columns A, C and B. After passing through the molecular sieve crystals in column B, the purified butadiene was introduced into a polymerization reaction vessel containing polystyryl lithium anions and polymerized.

The resulting reaction product was analyzed on a Gel Permeation Chromatograph using polystyrene standards and was found to contain about 2.3% by weight "dead" polystyrene.

The above data demonstrates the marked improvement in the reduction of dead polymer obtained using the method of this invention as compared to the prior art method.

It will be evident from the foregoing, that various modifications can be made to the present invention. Such, however, are considered as being within the scope of the invention.

What is claimed is:

1. In a method of purifying rubber grade diene monomers for anionic polymerization of the type wherein a rubber grade diene monomer is sequentially passed through molecular sieves and then adsorption alumina just prior to being introduced into the polymerization reaction vessel, the improvement comprising: purifying the rubber grade diene monomer by sequentially passing it through molecular sieves, then through adsorption alumina, and then through molecular sieves before introducing the purified rubber grade diene into the polymerization reaction vessel, said molecular sieves being selected from the group consisting of 3A and 4A type molecular sieves.

* * * * *